(12) United States Patent
Volpe et al.

(10) Patent No.: US 9,398,859 B2
(45) Date of Patent: *Jul. 26, 2016

(54) WEARABLE MEDICAL TREATMENT DEVICE WITH MOTION/POSITION DETECTION

(71) Applicant: ZOLL MEDICAL CORPORATION, Chelmsford, MA (US)

(72) Inventors: Shane S. Volpe, Saltsburg, PA (US); John D. Macho, Farmington, PA (US); Wade Braden, Pittsburgh, PA (US); Thomas E. Kaib, North Huntingdon, PA (US); Marshal W. Linder, New Kensington, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 78 days.

This patent is subject to a terminal disclaimer.

(21) Appl. No.: 14/180,775

(22) Filed: Feb. 14, 2014

(65) Prior Publication Data
US 2014/0163334 A1      Jun. 12, 2014

Related U.S. Application Data

(63) Continuation of application No. 12/840,633, filed on Jul. 21, 2010, now Pat. No. 8,676,313, which is a continuation of application No. 12/002,469, filed on Dec. 17, 2007, now Pat. No. 7,974,689.

(60) Provisional application No. 60/934,404, filed on Jun. 13, 2007.

(51) Int. Cl.
*A61B 5/0205* (2006.01)
*A61B 5/0404* (2006.01)
(Continued)

(52) U.S. Cl.
CPC ............. *A61B 5/0205* (2013.01); *A61B 5/0404* (2013.01); *A61B 5/044* (2013.01);
(Continued)

(58) Field of Classification Search
CPC .. A61B 5/0404; A61B 5/1117; A61B 5/1123; A61B 5/1118; A61B 5/6805; A61B 5/0205; A61B 5/04085; A61B 5/044; A61B 5/4836; A61B 5/1116; A61B 5/721; A61B 5/045; A61B 2560/045; A61B 5/7282; A61N 1/39; A61N 1/046

See application file for complete search history.

(56) References Cited

U.S. PATENT DOCUMENTS 4,094,310 A    6/1978   McEachern et al.
4,632,122 A    12/1986  Johansson et al.
(Continued)

FOREIGN PATENT DOCUMENTS

EP    0295497 B1    9/1993
EP    0335356 B1    3/1996
(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.
(Continued)

*Primary Examiner* — Catherine Voorhees
(74) *Attorney, Agent, or Firm* — Lando & Anastasi, LLP

(57) ABSTRACT

A wearable defibrillator consists of a vest (or belt) which is worn by the patient. The device monitors the patient's ECG with sensing electrodes and can monitor other patient conditions and in appropriate cases can treat certain conditions. An accelerometer(s) in the wearable defibrillator can allow for the device to determine the position, movements, forces applied to the patient, and/or the device. The device can use a least one patient motion detector generating a signal indicative of patient activity. Analysis of the signal can be indicative of patient activity appropriate for treatment or indication of device condition.

11 Claims, 5 Drawing Sheets

Accelerometer Positioning

(51) Int. Cl.
  *A61B 5/11* (2006.01)
  *A61B 5/00* (2006.01)
  *A61N 1/39* (2006.01)
  *A61B 5/0408* (2006.01)
  *A61B 5/044* (2006.01)
  *A61N 1/04* (2006.01)

(52) U.S. Cl.
  CPC ........... *A61B5/04085* (2013.01); *A61B 5/1116* (2013.01); *A61B 5/1117* (2013.01); *A61B 5/1118* (2013.01); *A61B 5/1123* (2013.01); *A61B 5/4836* (2013.01); *A61B 5/6805* (2013.01); *A61B 5/7282* (2013.01); *A61N 1/046* (2013.01); *A61N 1/39* (2013.01); *A61B 5/721* (2013.01); *A61B 2560/045* (2013.01)

(56) References Cited

U.S. PATENT DOCUMENTS

| | | |
|---|---|---|
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,330,505 A | 7/1994 | Cohen |
| 5,348,008 A | 9/1994 | Bornn et al. |
| 5,357,696 A | 10/1994 | Gray et al. |
| 5,365,932 A | 11/1994 | Greenhut |
| 5,564,429 A | 10/1996 | Bornn et al. |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,065,154 A | 5/2000 | Hulings et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,406,426 B1 | 6/2002 | Reuss et al. |
| 6,681,003 B2 | 1/2004 | Linder et al. |
| 6,690,969 B2 | 2/2004 | Bystrom et al. |
| 6,790,178 B1 | 9/2004 | Mault et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,908,437 B2 | 6/2005 | Bardy |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,220,235 B2 | 5/2007 | Geheb et al. |
| 7,277,752 B2 | 10/2007 | Matos |
| 7,295,871 B2 | 11/2007 | Halperin et al. |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,831,303 B2 | 11/2010 | Rueter et al. |
| 7,974,689 B2 * | 7/2011 | Volpe et al. ............ 607/6 |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,649,861 B2 * | 2/2014 | Donnelly et al. ............ 607/6 |
| 2003/0004547 A1 * | 1/2003 | Owen et al. ............ 607/5 |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0007970 A1 | 1/2004 | Ma et al. |
| 2004/0049233 A1 | 3/2004 | Edwards |
| 2005/0049515 A1 | 3/2005 | Misczynski et al. |
| 2005/0131465 A1 | 6/2005 | Freeman et al. |
| 2006/0036292 A1 | 2/2006 | Smith et al. |
| 2006/0085049 A1 | 4/2006 | Cory et al. |
| 2006/0178706 A1 | 8/2006 | Lisogurski et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0058884 A1 | 3/2008 | Matos |
| 2008/0249591 A1 | 10/2008 | Gaw et al. |
| 2008/0306562 A1 | 12/2008 | Donnelly et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0179438 A1 | 7/2010 | Heneghan et al. |
| 2010/0234716 A1 | 9/2010 | Engel |
| 2010/0295674 A1 | 11/2010 | Hsieh et al. |
| 2010/0298899 A1 * | 11/2010 | Donnelly et al. ............ 607/6 |
| 2010/0312297 A1 | 12/2010 | Volpe et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0158075 A1 | 6/2012 | Kaib et al. |
| 2014/0163334 A1 | 6/2014 | Volpe et al. |

FOREIGN PATENT DOCUMENTS

| | | |
|---|---|---|
| EP | 1455640 B1 | 1/2008 |
| EP | 1720446 B1 | 7/2010 |
| JP | 5115450 A | 5/1993 |
| JP | H11319119 A | 11/1999 |

(56) References Cited

FOREIGN PATENT DOCUMENTS

| | | |
|---|---|---|
| JP | 2002-102361 A | 4/2002 |
| JP | 2002200059 A | 7/2002 |
| WO | 0002484 A1 | 1/2000 |
| WO | 2004054656 A1 | 7/2004 |
| WO | 2006050235 A1 | 5/2006 |
| WO | 20070057169 A1 | 5/2007 |
| WO | 2007077997 A1 | 7/2007 |
| WO | 2010014497 A1 | 2/2010 |
| WO | 2010025432 A1 | 3/2010 |

OTHER PUBLICATIONS

DeBock et al., "Captopril treatment of chronic heart failure in the very old," J. Gerontol. (1994) 49: M148-M152.

International Search Report dated Nov. 21, 2011 from corresponding International Application No. PCT/US11/43360.

O'Keeffe et al., "Reproducability and responsiveness of quality of the assessment and six minute walk test in elderly heart failure patients," Heart (1998) 80: 377-382.

Search Report and Written Opinion from French counterpart application No. 0853856, dated Jan. 4, 2011.

\* cited by examiner

Figure 1: Accelerometer Positioning
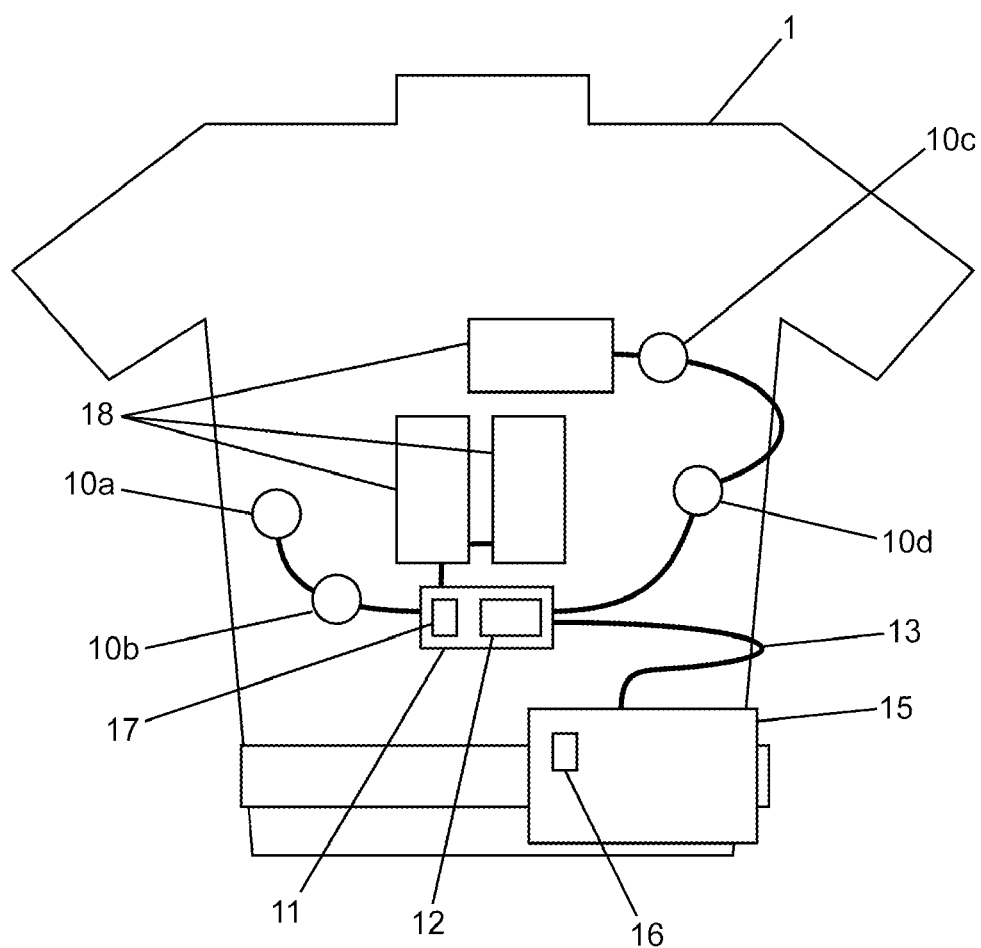

Figure 2: System diagram with accelerometers
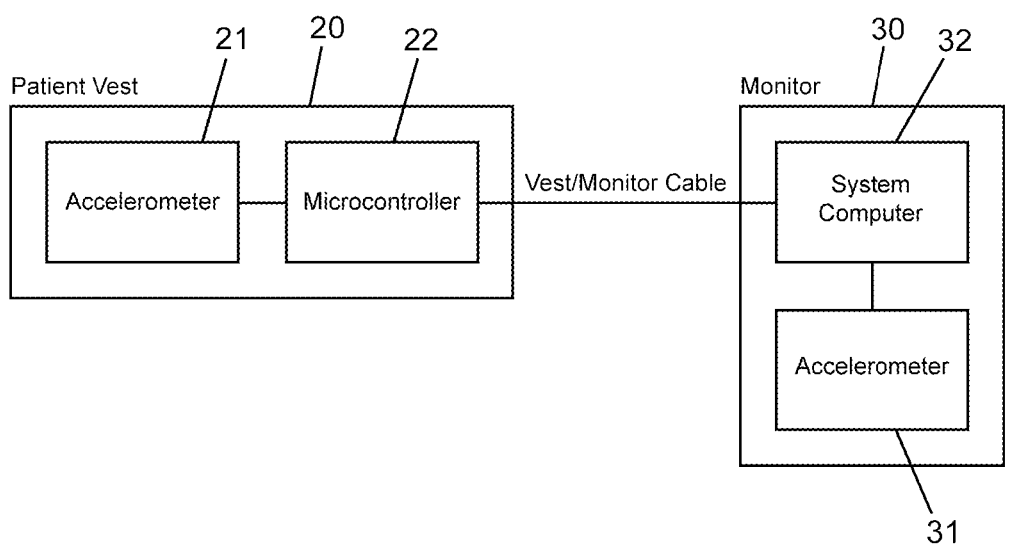

Figure 3: Monitor Accelerometer
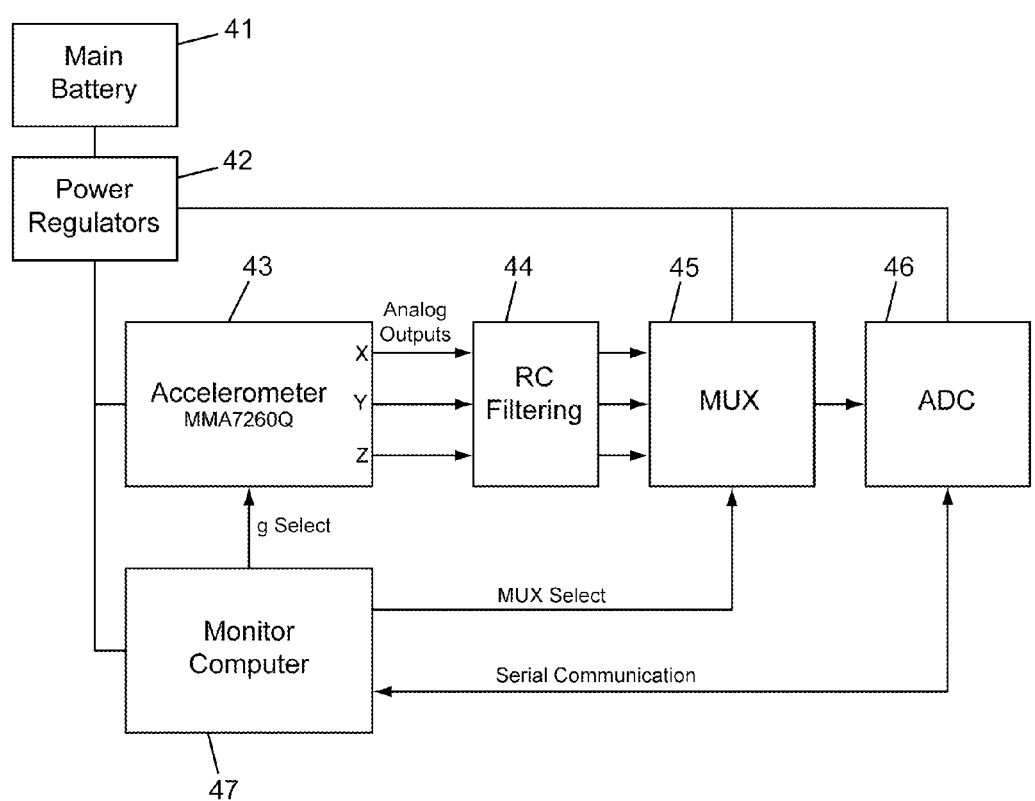

Figure 4: Belt Node Accelerometer
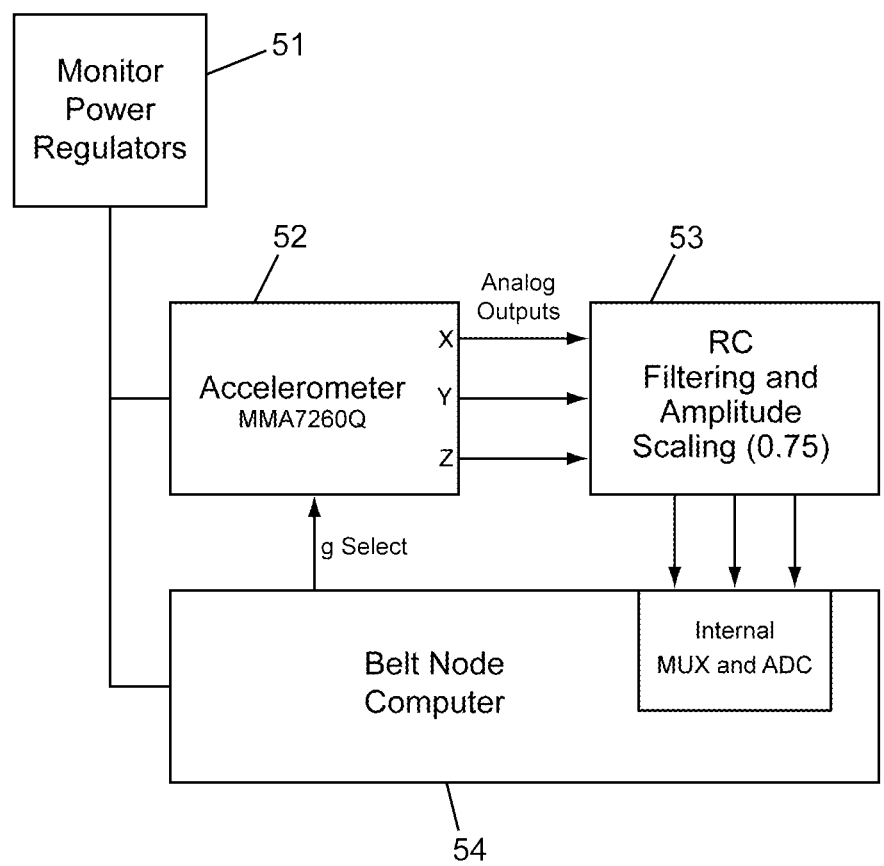

Figure 5: Arrhythmia Detection Algorithm Logic Diagram
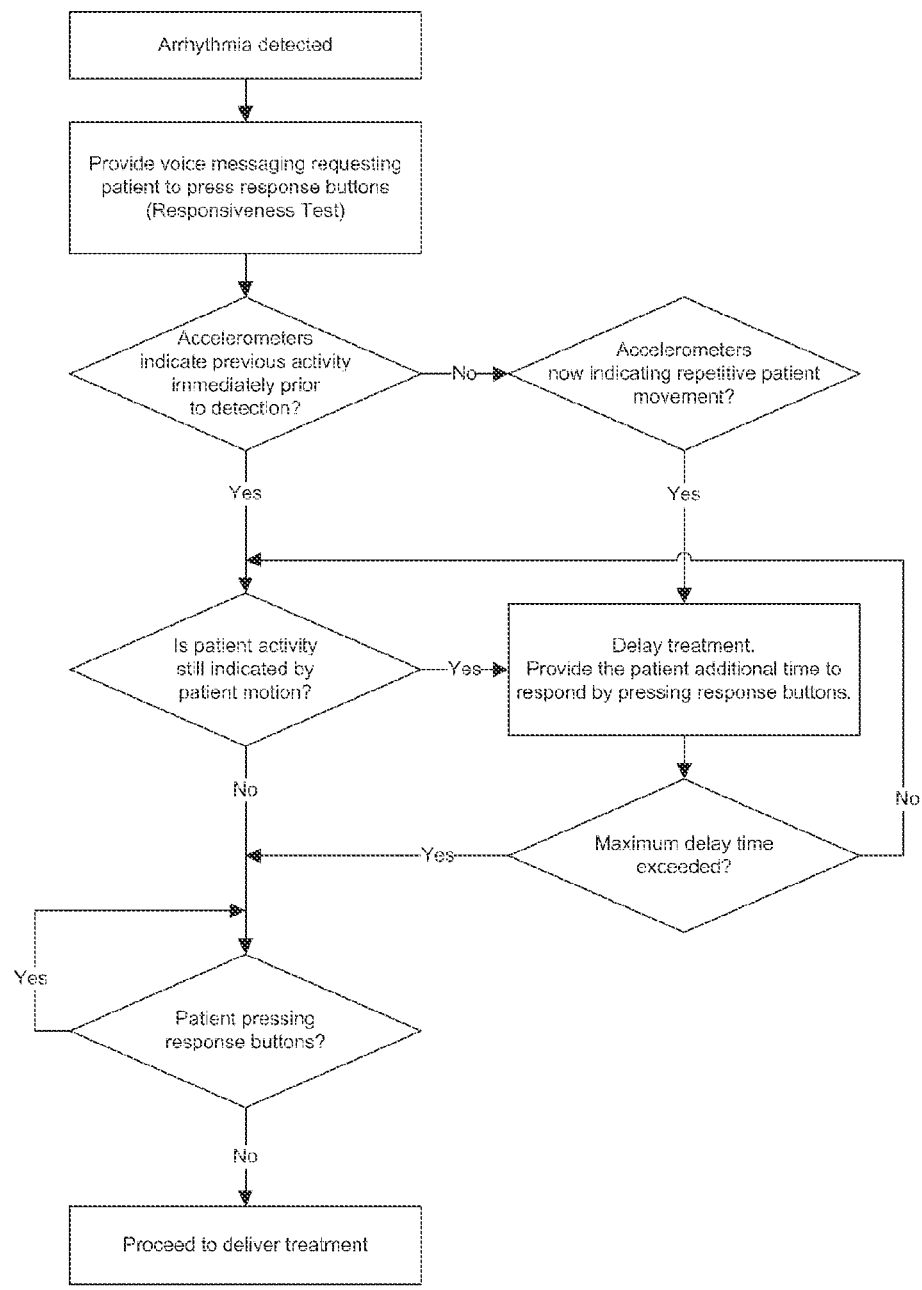

WEARABLE MEDICAL TREATMENT DEVICE WITH MOTION/POSITION DETECTION

CROSS-REFERENCE TO RELATED APPLICATIONS

This application is a Continuation of U.S. patent application Ser. No. 12/840,633, titled "Wearable Medical Treatment Device With Motion/Position Detection," filed on Jul. 21, 2010, which is incorporated herein by reference in its entirety. U.S. patent application Ser. No. 12/840,633 is a continuation of U.S. patent application Ser. No. 12/002,469 (now U.S. Pat. No. 7,974,689) titled "Wearable Medical Treatment Device With Motion/Position Detection", filed on Dec. 17, 2007, which is hereby incorporated herein by reference in its entirety. U.S. application Ser. No. 12/002,469 claims the benefit of U.S. Provisional Patent Application Ser. No. 60/934,404 titled "Wearable Medical Treatment Device With Motion/Position Detection", filed on Jun. 13, 2007. The following U.S. patents are hereby incorporated by reference: U.S. Pat. Nos. 4,928,690, 6,065,154, 5,944,669, 5,741,306, 6,681,003, 6,253,099, and 5,078,134.

FIELD OF THE INVENTION

The present invention is directed toward wearable defibrillators and, more particularly, toward wearable defibrillators capable of detecting the motion and/or position of a patient wearing the wearable defibrillator and using the sensed motion and/or position to determine an appropriate treatment.

BACKGROUND OF THE INVENTION

The wearable defibrillator consists of a monitor and a vest (or belt) which are both worn by the patient. The device monitors the patient's ECG with sensing electrodes, such as 10a, 10b, 10c, 10d, to detect life-threatening arrhythmias and delivers a cardioverting or defibrillating shock through therapy pads, such as 18, if treatment is needed.

There is also a third piece of equipment called the battery charger that can provide two functionalities: first it can charge the monitor batteries, 41, and second it can provide a gateway for the monitor to download data to a central server. The monitor can communicate to the charger through a wireless Bluetooth link and the charger can connect to a central server through the internet.

The accelerometer(s) can allow for the computer in the wearable defibrillator to determine the position of the monitor, belt and/or patient, and the corresponding applied forces. This information can be used in a confidence based arrhythmia detection algorithm to accelerate the timing to hasten the occurrence of or hold off therapy based on past and present body motion and/or position history.

Other devices that could be used instead of an accelerometer would include, but are not limited to: gyroscope, magnetometer, hall-effect devices, and other force motion or position sensors.

SUMMARY OF THE INVENTION

Accelerometers are able to measure x, y, and z positions. This improvement covers having an accelerometer in either the belt, which is worn on the patient's upper body, or in the monitor, which is worn on the patient's lower body; or both locations; or other positions on the patient.

The accelerometer in the belt can be used to determine patient position since it is located on the upper torso of the patient. As a result, the belt accelerometer will be chosen such that high sensitivity data can be measured or determined from possible body positions (e.g. patient position). The accelerometer in the monitor can be chosen so that high sensitivity data (such as breathing or other minor motion) can be measured; low sensitivity data (such as mechanical shock) can also be measured; or both. Additional accelerometers can also be used so that both low sensitivity and high sensitivity data can be measured, or an accelerometer capable of both low sensitivity and high sensitivity can be used.

Some embodiments of the invention include a patient wearable treatment device having treatment elements adjacent to said patient in proximity to said patient's skin, and at least one patient motion detector connected to the device and generating a signal indicative of patient activity, and at least one control to evaluate signals from said motion detectors to determine if said signal is indicative of patient activity appropriate for treatment.

Embodiments include using at least one accelerometer including at least one multi-axis accelerometer and can include two three-axis accelerometers with one of said accelerometers mounted on a patient vest portion and another of said accelerometers is mounted on the monitor or other portion. Some embodiments can include a visual display on said monitor portion where the orientation of said visual display is controlled by the output of said accelerometer.

The body orientation of the patient is determined by the output of at least one accelerometer including standing and prone.

Treatment can be accelerated or delayed based upon the output of the motion detector.

The invention can detect a patient condition based upon the level of activity of a patient over a period of time based upon said stored output of said accelerometer, and can be used to detect conditions such as, for example, congestive heart failure or sleep disorders.

A method of cardiac treatment of a patient including sensing a cardiac condition, sensing patient motion with sensors such as, for example, accelerometers worn by said patient and evaluating said sensed patient activity to determine treatment is appropriate to said cardiac condition.

Embodiments can detect vertical and prone positions and determine a patient activity and a patient body orientation.

The following is a list of the functionality, information that can be provided by the motion detection or accelerometers:

Patient body state: Patient is vertical, Patient is horizontal (On left side, On right side).

Patient is moving in repetitive pattern: Vibrating (environmental), Convulsing.

Patient is accelerating: Patient is falling.

Equipment (belt and monitor) state: x/y/z position.

Equipment acceleration.

Equipment mechanical shock (high force impact, acceleration).

Verification of tactile motor operation in belt node.

BRIEF DESCRIPTION OF FIGURES

FIG. 1 shows a diagrammatic representation of accelerometer positioning in certain embodiments with cardiac sensors and treatment electrodes.

FIG. 2 is a block diagram of an embodiment using two accelerometers.

FIG. 3 is a block diagrammatic representation of an embodiment using an accelerometer in a monitor.

FIG. 4 is a block diagram of one embodiment using a belt node accelerometer.

FIG. 5 is a logic diagram of an algorithm that can be used with one embodiment of the invention.

DESCRIPTION OF SOME EMBODIMENTS OF ALGORITHMS AND METHODS OF USING INFORMATION

FIG. 1 shows a patient 1 with a wearable defibrillator. Typically the devices shown would be worn as a vest, belt and/or other clothing. In this embodiment, four sensing electrodes 10a, b, c, d, or sensors are shown. While this embodiment is for cardiac monitoring and treatment, other medical functions could also be appropriately monitored or treated. In this embodiment, a node, 11, is used and the sensors 10a, b, c, d and treatment devices 18 connect to the node. The node 11 could be on the belt or on other patient locations. The therapy pads or treatment devices 18 provide treatment when a sensed condition indicates a preferred treatment.

Any motion sensor can be used. In the present preferred embodiment accelerometers are used. Such sensors indicate accelerating movements. Because of the nature of human movements, generally comprising short distance and short duration, accelerometers give a very acceptable indication of patient movement. Single axis accelerometers can be used as well as multi-axis sensors.

In this embodiment, two accelerometers 16, 17 are used. One accelerometer 17 is located on the node device 11 and a second 16 is used on the monitor 15. It is understood that some embodiments will use a single accelerometer or position/force/motion detector, and still other embodiments may use three or more. Using multiple sensors permit the treatment algorithm to evaluate accelerometer (sensor) differentials to predict patient activity and accelerometer reliability. The use of multiple accelerometers permit separate evaluation of different patient movements and comparing such separate movements to best determine patient activity and equipment function. The actual treatment algorithm used will usually depend upon the diagnostic requirement of each individual doctor and the condition(s) he wishes to monitor. Any or all of the activities determined by the invention can be used. These can be combined with other inputs.

FIG. 2 shows a block diagram of a device in which the accelerometer and microcontroller are housed on the patient, 1, wearable vest or belt. The vest worn devices can communicate via a cable or wireless communication link to a monitoring device that contains a second accelerometer 31. Each accelerometer 21, 31 can indicate the respective movement of its position of the patient, and/or be used in an algorithm that uses the combined signals to more reliably indicate patient activity. Processing of accelerometer data can be performed by the microcontroller 22 in the belt/vest node 20 or a system computer 32 located in the monitor 30 or at both processing locations. Accelerometers 21, 31, indicate change in velocity. Patients will normally have an activity level when conscious that includes changes in both velocity and direction. This is in contrast to the lack of change of body motion present in an unconscious patient. Other sensors such as, for example, gyroscopes can be used, with appropriate software to indicate motion or lack of motion. Outputs from sensors may be integrated, compared or differentiated to best predict patient activity, and reduce interference or error signals.

Patient Movement During Arrhythmia

The use of accelerometers can be used to determine a patient's body state during the detection of an arrhythmia. It also may be used to detect if a mechanically noisy environment is the cause of an erroneous arrhythmia detection.

Patient Movement Used in the Confidence Algorithm Factor

A confidence algorithm, which is influenced by many inputs including the patient's body state as determined by the accelerometers, is used to determine if a patient's heart arrhythmias requires defibrillation.

Generally, cardiac treatment is not required if the patient is conscious. By using accelerometers the patient body state can be monitored. If there has been no change in patient body state for a period of time as detected by the accelerometer(s) then there will be an increased confidence of the algorithm that the patient is unconscious. If a change in patient body state has been detected by the accelerometer(s) then there will be a decreased confidence of the algorithm that the patient is unconscious. The wearable defibrillator can hasten its decision to apply treatment if a high level of confidence exists that the patient is unconscious. If patient motion is detected while other sensors and algorithms indicate that a treatable rhythm is present, treatment delivery can be delayed to provide the patient additional time to respond to system messaging.

False Arrhythmia Detection Due to Physical Motion

Sometimes a false arrhythmia is detected by the system due to physical motion, i.e. electrode or cables moving against the body or clothing, which creates false deviations in the patient's ECG. If an arrhythmia is detected and vibration or high patient/equipment acceleration is detected then the patient can be alerted to this condition. The tactile stimulator may be turned on or the audio volume may be increased to notify the patient reference 1. This information may also be applied to the treatment confidence algorithm thereby causing a decrease in confidence given that the physical motion can cause a false positive detection. Use of the accelerometer (s) can reduce undesired treatment of false arrhythmias.

Correlation of ECG Artifact with Belt Motion

Motion of the electrode belt may cause interference with ECG signal pickup and possible false detections. The signals obtained from the accelerometer can be correlated with an ECG signal to determine if ECG signal contamination exists. The quality of the correlation can be used as an additional confidence factor in the arrhythmia detection algorithm. If an arrhythmia is detected and there is a high degree of correlation between the ECG signal and the accelerometer signal the confidence in the arrhythmia detection can be reduced. No signal correlation indicates increased confidence that the arrhythmia detection is accurate.

Treatment Verification

The accelerometers may also be used to verify that a treatment has been applied by detecting sudden movements or muscle spasms in a patient immediately following the treatment. Often after defibrillation a patient's muscles spasm from the energy pulse. The muscle spasm will cause detectable movements on the accelerometers similar to convulsing.

Detection of Bystanders/Unsuccessful Defibrillation

Post shock motion of the patient after several unsuccessful defibrillation attempts may indicate the presence of bystanders. The bystanders could be rescue personnel such as an EMT. In this case special alarms or voice messages could be generated to inform the bystander of the equipment and treatment status. Additional shocks could be delayed or cancelled to prevent a shock to the bystanders or rescue personnel.

Post Shock Motion Detection

When a shock is delivered the patient may move suddenly and then return to a state where there is a lack of motion. If no further motion is detected a high confidence can exist that the arrhythmia is still present. This information can be used as an additional post-shock confidence factor for the detection algorithm and that a continuing condition exists. If post-shock motion continues or if the patient body position changes from a horizontal to vertical position, there is high confidence that the defibrillation was successful and additional shocks can be delayed.

Belt Quality Feedback

Overall belt quality can be examined by gathering data using the accelerometers during certain failure states such as electrode fall-off and therapy pad fall-off detection.

Reduce Electrode and Therapy Pad Fall-Offs

If one of the electrodes 10 or therapy pads 18 fall off of the patient, then the system will record the patient body state during the fall-off event. Patient positions include sitting up, lying down; left side, right side. If vibration or patient falling is detected then that would also be recorded as well since it might be the cause of the falloff event.

Over time the data can be analyzed and used to determine positions that may tend to cause fall-offs. This information can then be used to improve the belt design reducing and possibly eliminating the fall-offs in those certain activities or positions.

An example would be if post analysis of data over a several month period of time shows that 75% of ECG fall-offs occur when the patient is laying on their left side then the belt design on the left side could be examined to determine what might be making it susceptible to fall-offs in that patient position.

Provide Recommendations to Patients

Accelerometers data collected over time could also be used to inform new patients of patient's body states that tend to be more comfortable. Patients who have worn the device for an extended time will most likely have experimented with different positions (sleeping positions, sitting positions, etc.) and will tend to use the most comfortable ones. This data can be recorded and used to improve the belt for the other positions and also provide recommendations to new patients.

Improve Belt Comfort

The accelerometer data collected during patient use can be used to improve the comfort of the belt by studying patient sleep habits, or habits during other selected activities.

If 80% of the patients tend to sleep on their right side then the assumption can be made that something about the belt makes it less comfortable for the patients to lie on their left side. With this information research can be performed to determine what about that position causes the belt to be uncomfortable and engineering can be performed to improve the belt comfort.

Belt Self Diagnostics

Self diagnostics may also be provided such as Belt Node Tactile Stimulator (vibration/acceleration) self test.

The tactile stimulator 12 (a patient notification device) is a motor with an unbalancing weight on its shaft. When the motor is on it causes the belt to vibrate much like a cell-phone in vibration mode.

When the tactile is activated the accelerometer 17 in the node can be used to verify that the node is vibrating which means that the tactile is working.

Patient Notification of Physical Events

The accelerometers can be used to provide feedback to the patient regarding certain mechanical events. They may also be used to adjust the device audio volume outputs based on the current state of the patient.

Equipment Abuse Notification

If certain mechanical conditions that may lead to equipment damage such as mechanical shock or vibration are detected by the accelerometers then the system can notify the patient of such conditions and advise the patient by the monitor computer screen on 15 of the condition.

If the monitor or belt is dropped or if they are hit with some other object causing a force greater than a predefined acceptable force, then the monitor will provide either an audio or visual (display) indication to the patient that the event has occurred and warn against allowing such an event to occur again.

If continuous vibration above a certain predefined acceptable threshold is detected for a period of time then the monitor on 15 may also provide a warning to the patient. Such vibration could lead to electrode or therapy pad fall-off or even cause false arrhythmia detection if enough physical motion is applied to the electrode and cables.

Adjust Device Alarm Volumes

If the accelerometers have recorded the patient body state to be unchanged for an extended time and the patient is either lying or sitting down then the monitor will assume the patient is sleeping and will then increase the audio volume output of any audio message if necessary to awaken the patient. The monitor may also enable the tactile stimulator to awaken the patient in the event of a critical audio message.

Adjust Display Rotation

The monitor accelerometer can be used to determine the proper rotation of the system display or LCD output on 15. The monitor 15 contains a display that can either be used to deliver a visual message to the patient or for initial patient setup by care givers. For patient visual messages, since the monitor is positioned approximately at the patient's mid section, the display would be upside down (rotated 180 degrees) with respect to the monitor. However, during patient setup, the monitor could be held right side up in front of the skilled personnel. As a result, the display would be right side up. The monitor accelerometer data can be used to adjust the display accordingly depending on how the display is attempting to be read.

Detect Equipment Abuse

Detect equipment abuse during use as well as during shipping. Equipment abuse can be determined by parameters such as number of times dropped and intensity. Detection of equipment abuse can trigger such actions as internal diagnostics, auto download, and equipment service recommendations.

Equipment Drop Detection

If the accelerometers detect a mechanical shock above a pre-determined acceptable threshold then the monitor will record a drop event. Other parameters such as date/time stamp and current operating mode will be recorded as well.

The date/time stamp should allow correlation between the monitor location and the damaging event allowing further information to be obtained using the carrier tracking numbers if such damage occurred during shipping.

If it is not during shipping and is during patient use and there is some form of equipment malfunction after the drop then that could be tied to the root cause of the equipment failure. Such information could be used to advice patients of the types of mechanical shocks that may damage the equipment. It also may be used to improve the robustness of the equipment to survive such forces in the future.

Equipment Service Recommendation

If the monitor accelerometer 16, belt accelerometer 17 have recorded a mechanical shock above a predefined acceptable threshold or if a predefined acceptable number of mechanical shocks has occurred then the monitor will recommend with an audio or visual (display) message via 15 to the patient that the equipment should be serviced. The monitor on 15 will also, during the next download, notify the manufacturer that it should be serviced.

Internal Diagnostics

If the accelerometer does detect an excessive mechanical shock on the belt or monitor then it may initiate internal self-diagnostics. Both the monitor 15 and node 11 have built-in circuitry as shown in FIGS. 3 and 4 to allow most of its components to be tested with self diagnostics.

Auto Download to Manufacturer

If there is a significant mechanical shock to the belt or monitor then the monitor may immediately initiate an automatic download to the manufacturer requesting service.

Monitor Patient Activity Over Time

Accelerometer data can be measured and stored over time to study patient activity. Patient activity data can be used to provide feedback to doctors about a patient's specific condition.

Patient Activity Data and Treatment

After a treatment event, patient activity data taken before, up to, and including the event can be downloaded. This data can be collected among patients and used to make correlations between patient activity derived from accelerometers 16, 17 and the probability of a possible treatment event occurring. These correlations can be used to take precautionary measures with patients who have similar activities as those who had past treatment events.

Patient Activity Data and Doctor Feedback

Patient activity data can be used over a period of time by doctors or data evaluation systems to determine if proper patient activity levels are met. Examples to study would be extremely low patient activity; patient performing recommended exercises; and/or patient real time activity level and corresponding heart rate data. Patients who are experiencing congestive heart failure can be monitored for physical activity and at rest body position. Gradual reduction in patient activity indicated by lack of motion can indicate a worsening of the congestive heart failure condition. Body position at rest can also indicate patient deterioration if body position at rest is primarily vertical since congestive heart failure patients may have difficulty resting in a horizontal position.

FIG. 1 shows the location of the accelerometers 16, 17 with respect to the patient and other system assemblies. The accelerometer 16 located in the front is the monitor accelerometer. The accelerometer located in the back is the belt node 17 accelerometer. The trunk cable 13 allows communication between the belt node computer and the main monitor computer in this embodiment. This permits belt node accelerometer data to be transferred to the main monitor computer 47. In addition, the trunk cable 13 allows monitor power supplies 41, 51 to be used to power the belt node computer and peripherals. The two accelerometers or motion detectors allow the system to determine parameters such as patient body position, patient body movement, patient body acceleration as well as perform certain system self-diagnostics. The monitor can contain either a high-G or a low-G accelerometer. A high-G low-sensitivity accelerometer would allow the system in addition to detect patient and equipment physical shock.

FIG. 3 shows the circuitry used to acquire data from the accelerometer 43 in the monitor (15 on FIG. 1). From the main battery 41, power regulators 42 are used to supply the electronics with needed voltages. The computer 47 controls various system parameters such as accelerometer sensitivity, multiplexer (MUX) 45 channel select, the analog to digital converter (ADC) 46, and serial communications. The Freescale Semiconductor MMA7260Q three axis low-g micromachined accelerometer can be used. The g-select control line between 47 and 43 allow the sensitivity to be varied from, for example, 1.5 g to 6 g. A high-G low sensitivity accelerometer could also be used instead of the MMA7260Q. This can allow patient/equipment shock to be detected. Resistor-capacitor (RC) filtering 44 can be used on each of the accelerometer outputs to minimize clock noise from the accelerometer internal switched capacitor filter circuit. The MUX 45 select lines can be controlled by the computer 47 and may allow each axis output of the accelerometer to be switched to the ADC 46 input. The ADC 46 can also be controlled by the computer 47 via a serial interface.

FIG. 4 is a block diagram that shows circuitry that can be used to acquire data from the accelerometer 52 on the belt node (11 on FIG. 1). Power supplies and regulators 51 derived from the monitor can be used to power the electronics in the belt node. The Freescale Semiconductor MMA7260Q three axis low-g micromachined accelerometer 52 can be used. The belt node computer 54 controls the g-select lines that again can allow the sensitivity to be varied from 1.5 g to 6 g. RC filtering as well as amplitude scaling 53 can be used on each of the accelerometer outputs. An internal MUX and ADC in the belt node computer 54 can allow the accelerometer analog outputs to be interfaced digitally directly to the computer.

An arrhythmia detection algorithm can be implemented by assigning various confidence coefficients or weighting values to the various detectors used by the algorithm. This can be done prior to using the motion detection confidence algorithm. For example, the monitor can be designed with two independent ECG data streams for analysis. The algorithm can execute independent algorithms on each data stream that analyze the signal to extract heart rate, morphology, frequency information, and other information. Additional analysis is performed, independently on each channel, to analyze the signal for noise contamination that may result from patient motion or biological signals such as muscle noise. Other secondary inputs to the basic detection algorithm can include a patient response button and inputs from the accelerometers.

A weighting value can be assigned to each detector, response button and accelerometer and the combination for all detectors can be used to make the decision that a treatable arrhythmia condition exists. In addition, the weighting values can be used to manipulate the timing of therapy delivery.

The action of the algorithm in the presence of a noisy ECG channel could be to place more weight on the heart rate detector in the clean ECG channel. For the accelerometer enhanced confidence algorithm, a weighting could be assigned that would delay delivery of treatment while patient motion is detected as shown in the flow diagram of FIG. 5.

The flow diagram in FIG. 5 shows that if patient motion is detected prior to the detection of a treatable arrhythmia, the timing of treatment delivery can be modified based on the accelerometer 16, 17 inputs when the arrhythmia is detected. If the patient becomes motionless coinciding with the arrhythmia detection, there is an increased confidence that the arrhythmia diagnosis is accurate and the delivery of treatment can occur sooner. If motion continues after the arrhythmia detection, the confidence of a valid detection can be decreased because lethal arrhythmias usually result in a lack of consciousness. In this case, the delivery of treatment can be delayed to allow time for audio voice messages to prompt the patient to respond by pressing the response button. The response button provides a responsiveness test input to the algorithm. In some embodiments, it may be desirable to never deliver a shock to a conscious patient. This algorithm can reduce the possibility of false treatment based on invalid rhythm diagnosis due to corrupt ECG inputs caused by excessive patient movement or other environmental factors.

FIG. 5 shows how a typical algorithm that detects arrhythmia can have an increased confidence by serially feeding through a subsequent confidence algorithm using input from a motion detector or accelerometer(s). Other motion detecting devices or confidence algorithms can use various motion detection criteria as desired by physicians and based upon the treatable condition or patient.

As it will usually be desirable to track and store data in the patient wearable device, the addition of motion data can also be stored, tracked and evaluated. One such use would be to evaluate historical motion/activity levels to detect conditions such as congestive heart failure. Such diseases are often found in patients who would be wearing a cardiac treatment device.

What is claimed is:

1. A wearable medical device comprising:
   cardiac sensing electrodes configured for external placement proximate to a patient and to sense cardiac information of the patient;
   at least one motion detector configured for external placement proximate to the patient to detect motion of the patient and a body position of the patient; and
   a monitoring computer coupled to the at least one motion detector and the cardiac sensing electrodes and configured to monitor the motion and the body position of the patient over a period of time, to detect changes in at least one of an amount of the motion and the body position of the patient over the period of time, and to determine whether the changes in the at least one of the amount of the motion and the body position of the patient over the period of time are indicative of congestive heart failure.

2. The wearable medical device of claim 1, wherein the at least one motion detector includes at least two three-axis accelerometers, with one of the at least two three-axis accelerometers mounted on a patient vest portion of the wearable medical device, and another of the at least two three-axis accelerometers mounted on a display portion of the wearable medical device.

3. The wearable medical device of claim 1, wherein the monitoring computer is configured to determine that the changes in the at least one of the amount of the motion and the body position of the patient over the period of time are indicative of congestive heart failure in response to detecting that the amount of the motion of the patient has decreased over the period of time.

4. The wearable medical device of claim 1, wherein the monitoring computer is further configured to determine that the changes in the at least one of the amount of the motion and the body position of the patient over the period of time are indicative of congestive heart failure in response to detecting that the body position of the patient has become more vertical over the period of time.

5. The wearable medical device of claim 1, wherein the monitoring computer is further configured to determine that the changes in the at least one of the amount of the motion and the body position of the patient over the period of time are indicative of congestive heart failure in response detecting that the amount of the motion of the patient has decreased over the period of time and the body position of the patient has become more vertical over the period of time.

6. The wearable medical device of claim 5, wherein the wearable medical device further includes at least one defibrillation electrode configured for external placement proximate to the patient to provide defibrillation treatment to the patient.

7. A method of diagnosing a patient comprising acts of:
   providing an externally wearable medical device including a plurality of cardiac sensing electrodes configured to be disposed adjacent the patient in proximity to the patient's skin, at least one motion detector configured to detect motion of the patient, and a monitoring computer coupled to the plurality of cardiac sensing electrodes and the at least one motion detector;
   sensing motion of the patient and a body position of the patient with the at least one motion detector over a period of time;
   detecting, in the monitoring computer, changes in at least one of the sensed motion and the sensed body position of the patient over the period of time; and
   determining, in the monitoring computer, whether the changes in the at least one of the sensed motion and the sensed body position of the patient over the period of time are indicative of congestive heart failure.

8. The method of claim 7, wherein the act of sensing includes sensing motion of the patient and a body position of the patient in multiple axes.

9. The method of claim 7, wherein the act of detecting includes detecting, in the monitoring computer, that an amount of the sensed motion has decreased over the period of time, and wherein the act of determining includes determining, in the monitoring computer, that the decrease in the amount of sensed motion over the period of time is indicative of congestive heart failure.

10. The method of claim 7, wherein the act of detecting includes detecting, in the monitoring computer, that the sensed body position of the patient has become more vertical over the period of time, and wherein the act of determining includes determining, in the monitoring computer, that the change in the sensed body position of the patient is indicative of congestive heart failure.

11. The method of claim 7, wherein the act of detecting includes detecting, in the monitoring computer, that an amount of the sensed motion has decreased over the period of time and that the sensed body position of the patient has become more vertical over the period of time, and wherein the act of determining includes determining, in the monitoring computer, that the decrease in the amount of sensed motion and the change in the sensed body position of the patient is indicative of congestive heart failure.

* * * * *